United States Patent
Goyal

(10) Patent No.: US 10,485,564 B2
(45) Date of Patent: Nov. 26, 2019

(54) SYSTEMS AND METHODS TO IMPROVE PERFUSION PRESSURE DURING ENDOVASCULAR INTERVENTION

(71) Applicant: MG STROKE ANALYTICS INC., Calgary (CA)

(72) Inventor: Mayank Goyal, Calgary (CA)

(73) Assignee: MG STROKE ANALYTICS INC., Calgary, Alberta (CA)

( * ) Notice: Subject to any disclaimer, the term of this patent is extended or adjusted under 35 U.S.C. 154(b) by 206 days.

(21) Appl. No.: 15/377,229

(22) Filed: Dec. 13, 2016

(65) Prior Publication Data
US 2017/0164963 A1 Jun. 15, 2017

Related U.S. Application Data

(60) Provisional application No. 62/267,160, filed on Dec. 14, 2015.

(51) Int. Cl.
*A61M 1/00* (2006.01)
*A61B 17/22* (2006.01)
*A61M 5/172* (2006.01)
*A61M 1/36* (2006.01)

(52) U.S. Cl.
CPC .......... *A61B 17/22* (2013.01); *A61M 1/3659* (2014.02); *A61M 5/1723* (2013.01); *A61B 2017/22079* (2013.01); *A61B 2017/22094* (2013.01); *A61M 1/00* (2013.01)

(58) Field of Classification Search
CPC .......... A61B 17/22; A61B 2017/22079; A61B 2017/22094; A61B 17/22001; A61M 1/00; A61M 1/3659; A61M 5/1723; A61M 1/1008
See application file for complete search history.

(56) References Cited

U.S. PATENT DOCUMENTS

2009/0024072 A1* 1/2009 Criado .................. A61M 25/10
604/9

* cited by examiner

*Primary Examiner* — Deanna K Hall
(74) *Attorney, Agent, or Firm* — McGlew and Tuttle, P.C.

(57) ABSTRACT

The invention relates to systems and methods to improve perfusion flow and pressure during endovascular intervention. In particular, the invention relates to catheters that enable both antegrade and retrograde flow through the catheter during a recanalization procedure and specifically at the step in a procedure where a clot is being withdrawn. Additionally, the invention provides systems for supplying fluids and fluid compositions to improve nutrition to ischemic brain.

6 Claims, 9 Drawing Sheets

SYSTEMS AND METHODS TO IMPROVE PERFUSION PRESSURE DURING ENDOVASCULAR INTERVENTION

FIELD OF THE INVENTION

The invention relates to systems and methods to improve perfusion flow and pressure during endovascular intervention. In particular, the invention relates to catheters that enable both antegrade and retrograde flow through the catheter during a recanalization procedure and specifically at the step in a procedure where a clot is being withdrawn. Additionally, the invention provides systems for supplying fluids and fluid compositions to improve nutrition to ischemic brain.

BACKGROUND OF THE INVENTION

Endovascular treatment of acute ischemic stroke is now the standard of care for patients with acute ischemic stroke due to large vessel occlusion in the anterior circulation. During various endovascular treatments, a surgeon will advance clot-retrieval or clot-suction devices into the brain's vasculature to the location of the clot where the clot is either withdrawn and/or aspirated from the clot site.

As is known, when a patient experiences a significant ischemic stroke event, those portions of the brain distal to the occlusion that experience a dramatic reduction in blood supply will affect the functioning of large regions of neurons. This reduction in blood supply may cause the patient to become symptomatic, cause the death of regions of the brain and/or put regions of the brain at the risk of dying if not treated quickly. Depending on the location and size of the occlusion will result a wide range of symptoms in the patient and depending on the severity will ultimately determine how a physician may choose to intervene or not.

It is well known that time delays in effecting treatment will typically result in the death of a greater number of neurons. Table 1 shows that in the specific case of acute ischemic stroke, the pace or rate of neural circuitry loss in a typical large vessel supratentorial acute ischemic stroke can be very rapid.

TABLE 1

Estimated Pace of Neural Circuitry Loss in Typical Large Vessel, Supratentorial Acute Ischemic Stroke
Estimated Pace of Neural Circuitry Loss in Typical Large Vessel, Supratentorial Acute Ischemic Stroke

|  | Neurons Lost | Synapses Lost | Myelinated Fibers Lost | Accelerated Aging |
|---|---|---|---|---|
| Per Stroke | 1.2 billion | 8.3 trillion | 7140 km/4470 miles | 36 yrs |
| Per Hour | 120 billion | 830 billion | 714 km/447 miles | 3.6 yrs |
| Per Minute | 1.9 million | 14 billion | 12 km/7.5 miles | 3.1 weeks |
| Per Second | 32,000 | 230 million | 200 meters/218 yards | 8.7 hours |

The numbers presented above represent an average and as understood there is a very high degree of variability based on the available blood supply to the ischemic region through collateral channels. However, as can be seen, delays in making a decision in the order of only a few minutes can have a significant impact on neural circuitry loss and ultimately patient outcome.

Moreover, a slight reduction in blood supply can tip the balance and dramatically further increase the rate of cell death.

In diagnosing and treating ischemic stroke, it is important for the physician to know where the vessel occlusion is, how big the occlusion is, where any dead brain tissue (termed "core") is and, how big and where is the brain tissue that may have been affected by the ischemic event but that may potentially be saved (termed "penumbra").

More specifically, the penumbra is tissue around the ischemic event that can potentially stay alive for a number of hours after the event by the perfusion of this tissue by collateral arteries. That is, the collateral arteries may provide sufficient oxygen, nutrients and/or flushing to the penumbra tissue to prevent this tissue from dying for a period of time.

Anatomical Variables

There are many anatomical considerations that can affect the severity and ultimately treatment of ischemic stroke. Importantly, as above, while a blood clot may severely affect blood flow to the ischemic area, some blood flow may get to the ischemic area if collateral arteries are functioning to at least partially perfuse the affected area.

The most common large vessel occlusion that is treated by endovascular techniques is the M1 segment of the middle cerebral artery (MCA). When a patient has an M1 occlusion, the territory supplied by the M1 receives a dramatic reduction in blood supply. As a consequence distal neurons don't function well and the patient becomes symptomatic. Preferably, there is some blood flow that manages to get to the ischemic territory through collaterals which may decrease the rate of neuronal death. Generally, in this case, the collaterals are the connections between the distal most branches of the anterior cerebral artery and the middle cerebral artery (or the posterior cerebral artery and the middle cerebral artery).

In different patients, collaterals are highly variable and there are a number of factors at play which are not fully understood. Some of these factors are genetic in nature but conditions such as hypertension and diabetes (and other poorly understood factors) may also reduce the efficacy of collaterals in different patients.

Importantly, regardless of the patient's anatomy, the maintenance of collateral blood flow is critical to keep the brain alive until the time the occluded vessel can be recanalized and blood flow re-established.

It is not well understood what keeps collaterals open but, amongst various factors, the pressure head in the vessel supplying the collaterals is considered important. In addition, systemic pressure and/or chemical factors that may be produced locally by the ischemic brain may also contribute.

In the case of an M1 occlusion, the collaterals between the anterior carotid artery (ACA) and the middle carotid artery (MCA) are likely kept open by the pressure in the ACA.

Other anatomical factors that may affect blood flow during a stroke including the effect of blood flow through the Circle of Willis (COW). FIG. 1 is a schematic diagram showing the major arteries within the cerebral vasculature and FIG. 2 is a schematic diagram showing variations in COW blood flow within the population which can affect collateral blood flow in the event of a stroke.

Importantly, the arrangement of the brain's arteries into the Circle of Willis creates redundancies in the cerebral circulation such that if one part of the circle becomes blocked or narrowed (stenosed) or one of the arteries supplying the circle is blocked or narrowed, blood flow from the other blood vessels can often preserve the cerebral perfusion well enough to avoid the symptoms of ischemia through collaterals. As shown in FIG. 2, there is significant variation between individuals' COW anatomy (both inherent and age related factors) such that an individual's COW anatomy can significantly affect collateral blood flow in the event of a stroke.

In particular, important connections at the COW include:
a. Anterior communication artery. This artery is the connection between the two anterior cerebral arteries (FIG. 1). The functionality of this part of the COW is dependent on the presence of good sized A1 segments of the anterior cerebral arteries as well.
b. Posterior communicating artery: This artery is a communication between the internal carotid artery (ICA) and the ipsilateral posterior cerebral artery (PCA). For good functionality of this part of the COW there also needs to be a good sized P1 segment of the PCA.

In a patient who has occlusion of the terminal ICA and M1 segment of the MCA, the only way for the anterior part of the MCA territory to stay alive is for the blood to come from the other ICA, go across the anterior communicating artery and finally through the ACA-MCA collaterals to supply the anterior part of the MCA territory. In such a patient if there is an insufficient COW, the brain tissue dies very quickly before any treatment can be administered.

Similarly in a patient who had a fetal PCA (PCA comes off the ICA with a hypoplastic or small P1 segment (FIG. 2), in the presence of a terminal ICA and M1 clot the posterior part of the MCA territory is unable to survive due to lack of filling of the MCA-PCA collaterals.

In patients with M1 occlusion, if the ICA is widely patent (there is no significant stenosis) and there is a good ipsilateral A1 segment, the collaterals are not dependent on the COW. However in such a situation, if there is a compromise in the flow through the ICA, the presence of a patent COW can compensate for the reduced pressure head in the distal ACA.

In most situations, the COW has potential connections that may have very little flow through it.

For example, it is quite common to have a hypoplastic A1 segment of the anterior cerebral artery in which case the distal ACA is primarily supplied through the anterior communicating artery from the contralateral side (FIG. 2B).

Other situations such as person's neck position can also influence flow through the COW.

Methodologies of Endovascular Thrombectomy and Effect on Collateral Flow

Broadly, there are two main techniques used for recanalizing an occluded vessel intracranially. The two of them can be used in conjunction with each other and include:
a. Stent Retriever—A stent retriever is a device comprising a compressed wire framework that is advanced to the clot within a catheter, whereupon reaching the clot, the stent retriever is unsheathed from the catheter allowing it to expand within the clot whereby the clot becomes entangled within the wire frame of the device, allowing the physician to withdraw the device with the clot entangled therein.
b. Aspiration—With this technique, a large bore catheter that is very flexible in negotiated by the physician to the level of the thrombus that is occluding the vessel. Once the catheter is close to the clot, negative (retrograde) pressure is applied either through a pump or manually such that the clot is aspirated through the catheter by the strong negative pressure.

Based on clinical experience and computational flow dynamics studies, it is generally understood that the presence of large bore catheters significantly affects collateral flow and pressure head in patients with 'relatively isolated' circulation and presence of M1 occlusion.

More specifically, the degree of flow and/or pressure reduction is influenced by:
a. ratio of a catheter diameter vs. parent vessel diameter.
b. size of alternative pathways (e.g. small Acom).
c. how distal the catheter is and its tortuosity within the vessels (e.g. a balloon guide catheter in the proximal ICA may be less obstructive than a DAC (distal access catheter) within the intracranial ICA). That is, the action of pushing a catheter through a small vessel having complex curvatures has an affect particularly as the catheter progresses further into the brain and the relative difference in size between the catheter and inner diameter of the vessel it is advancing through becomes smaller.
d. Other factors such as the systemic Blood Pressure may also contribute.

In addition, it also generally understood that applying suction (retrograde flow) further reduces the flow through collaterals as the negative pressure has the effect of reducing blood pressure in areas immediately surrounding where the negative pressure is being applied.

Accordingly, there has been a need for systems and methods that improve the flow of blood through collaterals that may be diminished as a result of endovascular treatment. In particular, there has been a need for systems and methods that maintain or enhance antegrade flow through the vasculature through which catheters may be progressing and/or maintaining antegrade flow at desired perfusion pressures while retrograde flow is active during clot removal.

Additionally, there has been a need for systems that can not only maintain the perfusion pressure but also improve nutritional delivery (oxygen, glucose etc) to the ischemic tissue. In addition there has been a need for systems that can improve flow by altering the physical characteristics of the blood (e.g. reduce viscosity).

SUMMARY OF THE INVENTION

In accordance with the invention, there is provided a system to maintain and/or enhance perfusion pressure in a patient with acute stroke and having relatively isolated circulation during an endovascular procedure as a catheter is advancing within the internal carotid artery, the system comprising: a catheter adapted for placement within the internal carotid artery, the catheter having a lumen enabling both antegrade and retrograde flow within the lumen, the catheter for operative connection to a pump and controller, the pump and controller for providing selective antegrade flow through the catheter and selective retrograde flow through the catheter at different times during an endovascular procedure where antegrade flow supports collateral perfusion and retrograde flow removes a clot.

In another embodiment, the system includes a fluid supply operatively connected to the pump and controller, where the fluid supply includes any one of or a combination of isotonic solutions supporting neuron viability including any one of or a combination of nutrient rich fluids, viscosity reducing fluids, free radical scavengers, neuroprotectants, blood and/or flushing agents.

In further embodiments, the controller has means for a. selectively providing antegrade flow through the catheter at a pressure to maintain perfusion pressure; and, b. selectively providing retrograde flow through the catheter at a pressure sufficient to hold and/or withdraw a blood clot through the catheter.

In other embodiments, the controller has means for: a. inputting any one of or a combination of: i. degree of isolation of circulation; ii. size of the patient's ICA; iii. size of the catheter; iv. size of a microcatheter within the catheter; v. degree of tortuousity of the patient's vasculature; vi. systemic blood pressure; and vii. properties of fluid being injected; b. calculating a flow rate of fluid through the catheter sufficient to maintain perfusion pressure based on data from step a; and, c. pumping the fluid into the catheter at a flow rate calculated in step ii.

In another aspect the invention provides a catheter to maintain and/or enhance perfusion pressure in a patient with acute ischemic stroke and having relatively isolated circulation during an endovascular procedure, the catheter comprising a double lumen catheter where a first lumen is adapted to provide retrograde flow through the first lumen and a second lumen is adapted to provide antegrade flow through the second lumen.

In one embodiment, the first and second lumens are concentric and the first lumen is centrally positioned relative to the second lumen.

In another embodiment, the catheter includes a distal tip and distal tip region and the distal tip region does not include the second lumen.

In yet further embodiments, the catheter has an outer wall between the exterior of the catheter and second lumen and the outer wall includes a plurality of exit ports between the second lumen and the exterior of the catheter allowing fluids to pass from the second lumen to the exterior of the catheter. In one embodiments, the exit ports are located adjacent the distal tip region are typically 10-25 cm from the distal tip.

In another aspect, the invention provides a method of maintaining perfusion pressure within an ischemic stroke patient during an endovascular procedure while a catheter is being advanced within the patient's vasculature, the method comprising the steps of: a. providing antegrade flow within a lumen of the catheter at a flow rate sufficient to maintain perfusion pressure within the patient's vasculature distal to the catheter.

In various embodiments, the method also includes the steps of: prior to step a. i. inputting any one of or a combination of: degree of isolation of circulation; size of the patient's ICA; size of the catheter; size of a microcatheter within the catheter; degree of tortuousity of the patient's vasculature; systemic blood pressure; and properties of fluid being injected; ii. calculating a flow rate of fluid through the catheter sufficient to maintain perfusion pressure; and, iii. pumping the fluid into the catheter at a flow rate calculated in step ii.

In further embodiments, the fluid being injected includes any one of or a combination of isotonic fluids supporting neuron viability including nutrient rich fluids, viscosity reducing fluids, free radical scavengers, neuroprotectants, blood (autologous or otherwise) and/or flushing agents.

In yet another aspect, the invention provides a method of maintaining perfusion pressure to an ischemic stroke patient while undergoing an endovascular procedure to remove a blood clot, the method comprising the steps of: a. providing antegrade flow within a lumen of the catheter at a flow rate sufficient to maintain perfusion pressure within the patient's vasculature distal to the catheter; and b. withdrawing and reinjecting blood from the patient during step a) into the catheter.

BRIEF DESCRIPTION OF THE DRAWINGS

Various objects, features and advantages of the invention will be apparent from the following description of particular embodiments of the invention, as illustrated in the accompanying drawings. The drawings are not necessarily to scale, emphasis instead being placed upon illustrating the principles of various embodiments of the invention. Similar reference numerals indicate similar components.

DETAILED DESCRIPTION OF THE INVENTION

With reference to the figures, systems and methods for providing or enhancing antegrade flow through a catheter during an endovascular procedure are described.

Introduction

Various aspects of the invention will now be described with reference to the figures. For the purposes of illustration, components depicted in the figures are not necessarily drawn to scale. Instead, emphasis is placed on highlighting the various contributions of the components to the functionality of various aspects of the invention. A number of possible alternative features are introduced during the course of this description. It is to be understood that, according to the knowledge and judgment of persons skilled in the art, such alternative features may be substituted in various combinations to arrive at different embodiments of the present invention.

Figure 3:
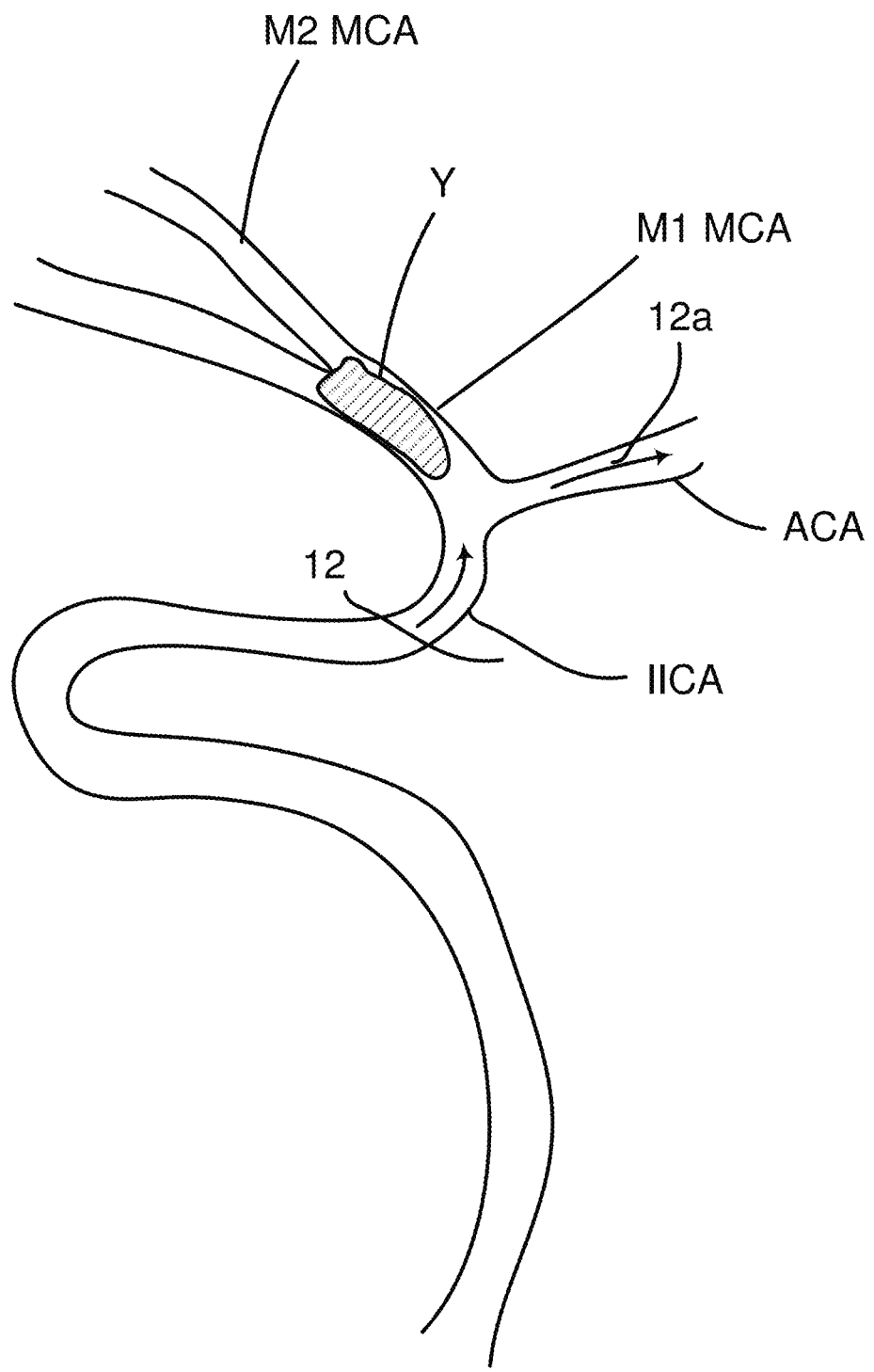
FIG. 3 is a schematic sketch of a portion of brain vascular anatomy showing the ophthalmic artery (OA), intracranial internal carotid artery (IICA), anterior cerebral artery (ACA), M1 segment of the middle cerebral artery and M2 segment of the middle cerebral artery.
Figure 4:
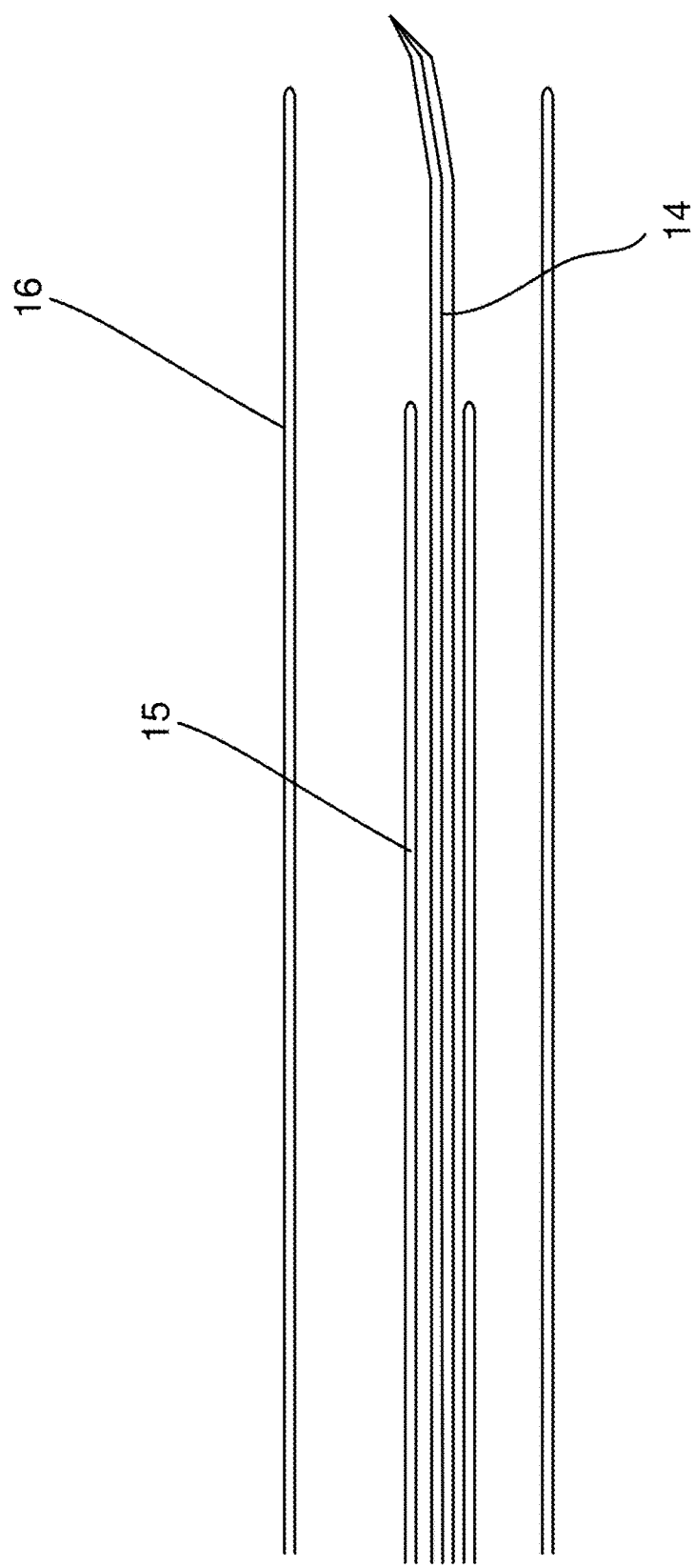
FIG. 4 is a sketch of a typical microwire, microcatheter and distal access catheter that may used for various recanalization procedures in accordance with the prior art.
Figure 5:
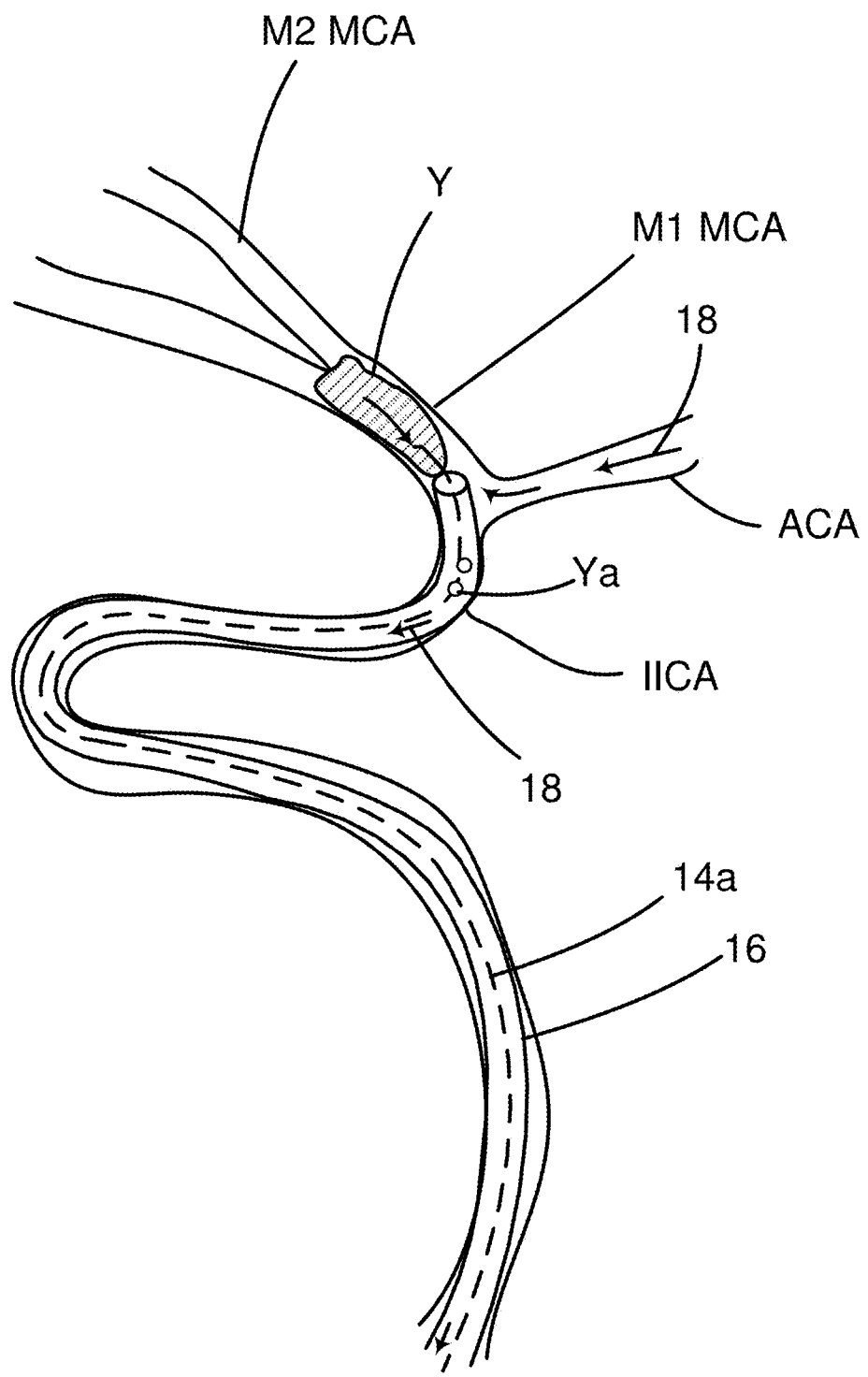
FIG. 5 is a sketch of a microwire, microcatheter and distal access catheter (DAC) in position adjacent a clot whilst conducting a recanalization procedure. For the purposes of illustration, the microcatheter and microwire appear substantially as a single element within this figure.

FIG. 3 is a schematic diagram of brain vascular anatomy showing the intracranial internal carotid artery (IICA), anterior cerebral artery (ACA), M1 segment of the middle cerebral artery and M2 segment of the middle cerebral artery. A clot Y is shown within the M1 MCA with arrow 12 showing the direction of blood flow prior to any procedure. For the purposes of discussion, it is understood that blood flow 12a through the ACA is supporting collateral perfusion to affected areas of the brain. FIG. 4 is a schematic cross-sectional diagram of a typical triaxial system including a distal access catheter (DAC), microcatheter and guide wire that may be used during a recanalization procedure. For the purposes of general description, the problem and solution of the present invention are described by a description of a typical clot aspiration procedure. During this procedure, the physician would typically complete the following general steps to remove the clot after gaining access to the femoral artery:

a. advance a microguide wire 14 to the clot (typically a 0.038" wire).
b. advance a microcatheter 15 over the microguide wire 14 to the clot Y.
c. advance a distal access catheter (DAC) 16 (may be termed a reperfusion guide catheter (RGC)) over the microcatheter 15 and microguide wire 14 to the clot Y.
d. withdraw the microcatheter and microguide wire 14. Turn aspiration on to the DAC, advance the DAC to engage the clot. a) If flow is observed through the DAC and the clot Y gets sucked out followed by blood, stop and check that the vessel is opened; alternatively, b) if there is no flow through the DAC, the clot may be stuck in the DAC or at the tip of the DAC in which case, wait a minute and withdraw the DAC while maintaining aspiration.

As is known, there are numerous variations in this type of recanalization procedure utilizing different clot retrieval or entrapment devices and/or the use of different catheters including balloon guide catheters that are temporarily inflated to occlude flow during the steps of a procedure when an entrapped clot is being withdrawn. Importantly, with each technique at one or more steps during the procedure, vessels are either occluded and/or retrograde flow is induced which has the effect of reducing pressure and the ability of non-occluded vessels to support effective collateral flow.

Figure 6:
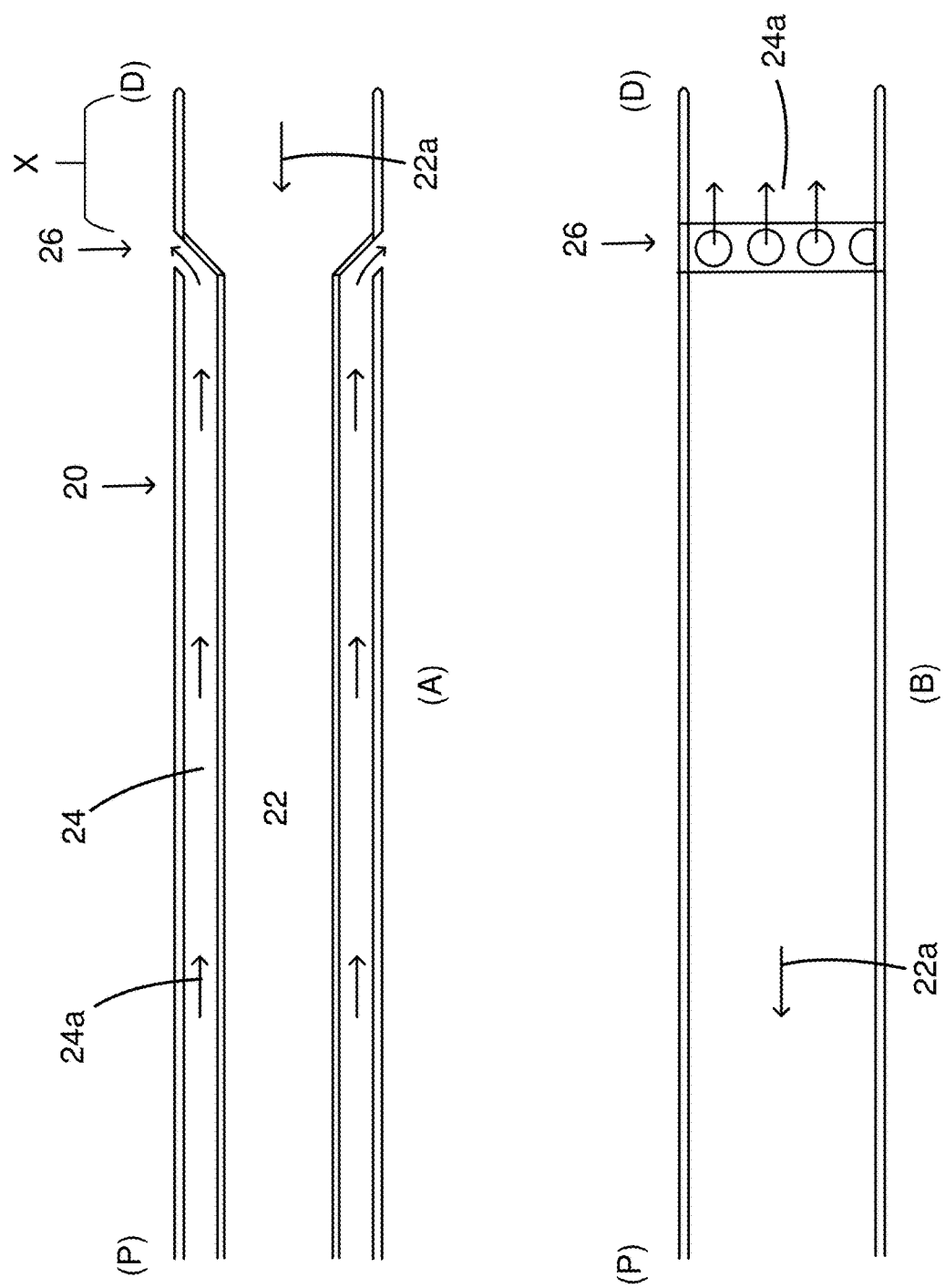
FIG. 6 are two schematic diagrams of a catheter having a first lumen enabling antegrade flow through the catheter and a second lumen enabling retrograde flow with (A) showing a cross-sectional view and (B) showing a side view.

With reference to FIG. 6 (A) and (B), a catheter 20 having the capability of providing antegrade flow during a recanalization procedure is described. Generally, the catheter 20 has an outer wall 20*a*, a proximal end P and a distal end D. As known to those skilled in the art, the total length of the catheter 20 may be 1-2 m and has an outer diameter of approximately 3 mm. As shown, the catheter has a first lumen 22 and a second lumen 24 radial and generally concentric with the first lumen. The first lumen 22 functions in the manner of a typical DAC used during a clot removal technique, that is a conduit to enable the passage of guide wires and/or other microcatheters to convey clot removal or retrieval equipment to the clot. In addition, the first lumen functions as a conduit to enable retrograde flow 22*a* from the clot site to outside the body during procedural steps where the clot is being physically removed.

The second lumen 24 functions to enable antegrade flow 24*a* through the catheter 20 during all steps of the procedure but importantly whilst retrograde flow 22*a* is initiated. As shown, the second lumen 24 does not progress the entire length of catheter 20 but includes at least one exit port 26 proximal and near the distal end D of the catheter (typically within 1-3 cm but may be as much as 10, 15 or 25 cm from the distal end D). As such, and as shown in FIG. 7, in one example, during procedural steps where retrograde flow is required to physically remove the clot Y, antegrade flow 24*a* is maintained through the second lumen 24 such that antegrade flow 24*a* can be maintained through the vasculature that may be useful or effective in ensuring vessel pressure to maintain collateral flow.

Figure 7:
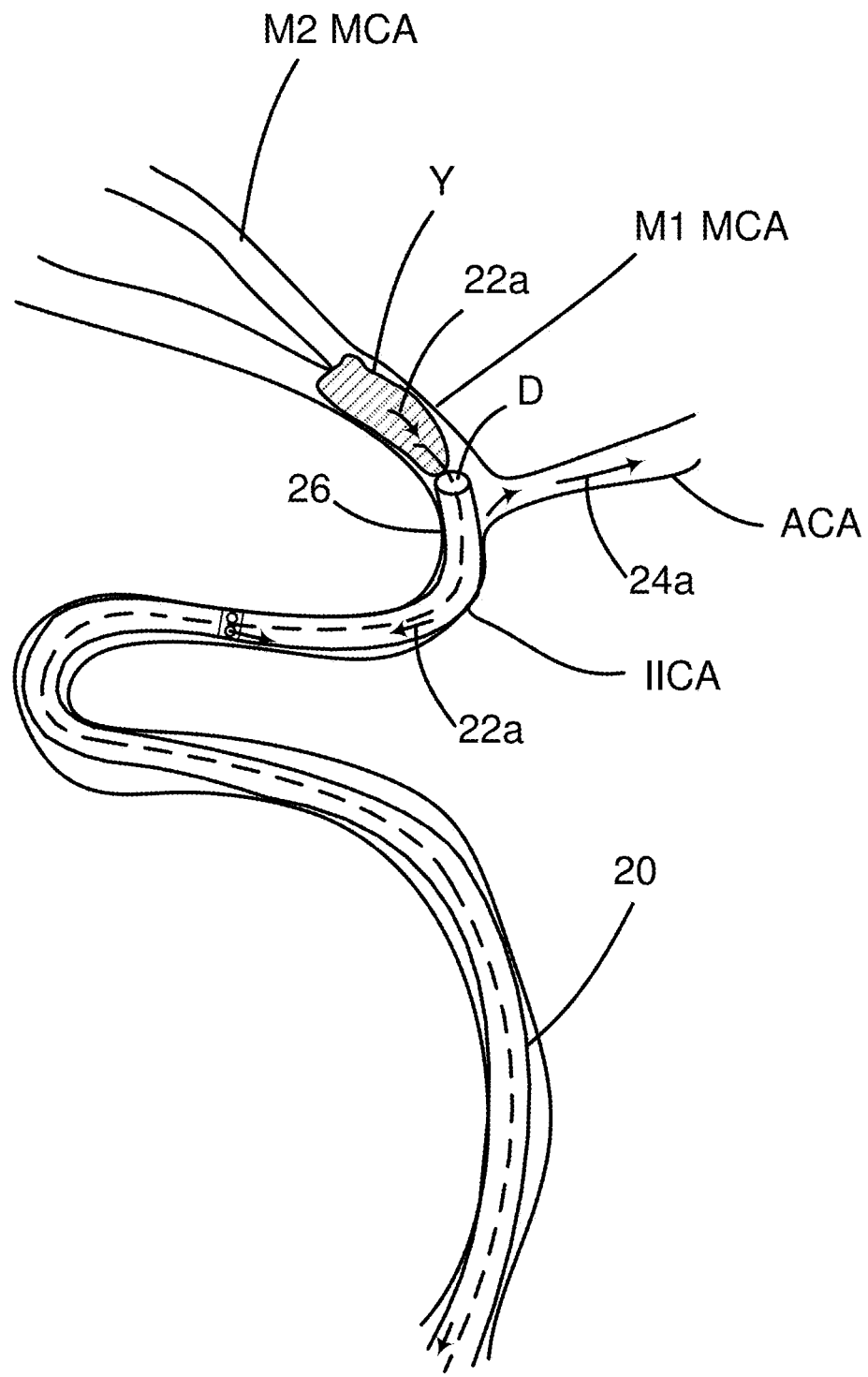
FIG. 7 is a sketch of a microwire, microcatheter and distal access catheter (DAC) in accordance with the invention showing antegrade flow through the catheter at a position proximal to the tip of the catheter and antegrade flow at the tip of the catheter.

That is, as shown in FIG. 7, the physician has initiated retrograde flow through the first lumen such that fluid/clot is being drawn into the distal end D of the catheter 20. As shown, the ACA is upstream of the clot Y and thus is able to receive antegrade flow emanating from the exit port 26 of the catheter 20. As such, pressure can be maintained within the ACA in this example.

it is important to note that in order to maintain sufficient flexibility in the tip of the DAC whilst the DAC is being advanced to the clot to prevent or minimize the risk of it being impossible to advance the catheter, that the second lumen ends some distance from the distal end D. That is, as noted above, the second lumen may end in the range of 10-25 cm from the distal end D. in embodiments where the distance X, is in this range, the tip region defined by X may be substantially more flexible than in the double lumen zone. Under appropriate fluid and pressure control, this embodiment will still enable appropriate antegrade flow of fluid into the vessels supporting collateral flow.

In an alternate embodiment, and as explained in greater detail below, a single lumen DAC is utilized as a source of antegrade flow during the initial stages of the procedure. In this case, as the DAC is being advanced, antegrade flow is maintained within the DAC. Antegrade flow will be terminated shortly before the tip of the DAC arrives at the clot whereupon retrograde flow is initiated as the DAC is advanced into the clot.

Figure 8:
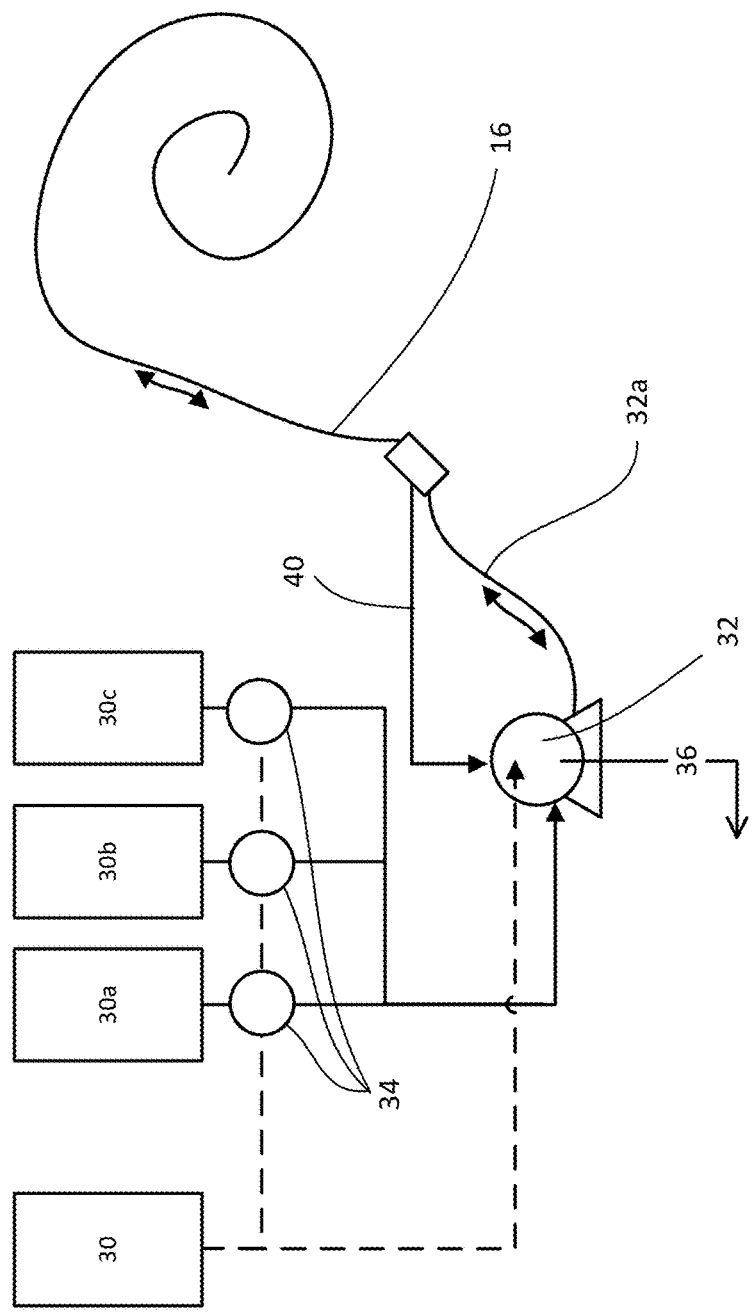
FIG. 8 is a schematic diagram of an integrated pump and control system operable to control the antegrade flow of fluids into the catheter.

As shown in FIG. 8, a pump 32 external to the body and operatively connected to catheter 16 (having one or first and second lumens) and a control system 30 and valves 32 supplying one or more nutrients or nutrient solutions 30*a, b, c* provide appropriate pressures and flow rates of fluids to achieve both antegrade flow to maintain pressure to support collateral flow and retrograde flow 36 for clot removal. Various parameters may be incorporated and considered by the control system to ensure correct flows and pressures. Such parameters may include the diameter of the parent vessel, the diameter of the DAC and/or pre-determined mathematical calculations to deliver fluid through the DAC such that the flow and pressure head in the collateral channels is minimized or unaffected.

The fluids that may be circulated through the catheter may themselves include properties to support collateral flow. Such properties may include low viscosity fluids to encourage increased flow through collaterals and/or nutrients such as glucose, oxygen, free radical scavengers and/or flushing agents that encourage the removal of metabolic by-products of neurons. In addition, fluids may include properties that reduce the viscosity of blood.

In one embodiment, the procedure can include the further step of introducing a colored fluid through the second lumen to guide the suction through the primary catheter. For example, if the fluid being injected is green and the return through the suction catheter is green, this may be an indicator to the physician that the clot is not engaged and most of the pressure is sucking the green fluid back, thus signaling the need to advance the DAC further to engage the clot.

In another aspect of the invention as introduced above, a regular DAC is provided, that is without a double lumen, and an external pump system controls an antegrade flow of fluid through the DAC as the DAC is being advanced towards the clot. In this case, the antegrade flow will assist the inherent antegrade pressure and flow of blood through the vessels that may be affected as result of the presence of the catheter in the vessels. This procedure may provide significant benefits to patients and particularly those where the physician may be experiencing difficult is moving the catheter into position. That is, depending on a patient's anatomy, which may be inherent or a result of age and other factors, the length of time to advance a catheter is typically in the range of 3-20 minutes where during this time, pressure and flow of blood to the collaterals may be affected. Thus, to the extent that a normal or moderately enhanced pressure arid antegrade flow can be maintained, this may improve the functioning of collaterals during the procedure over currently used procedures where during catheter placement no enhancement of pressure and flow is provided.

As noted above, the fluid pumped through the catheter may include friction reducing agents and/or various nutrients.

Figure 1:
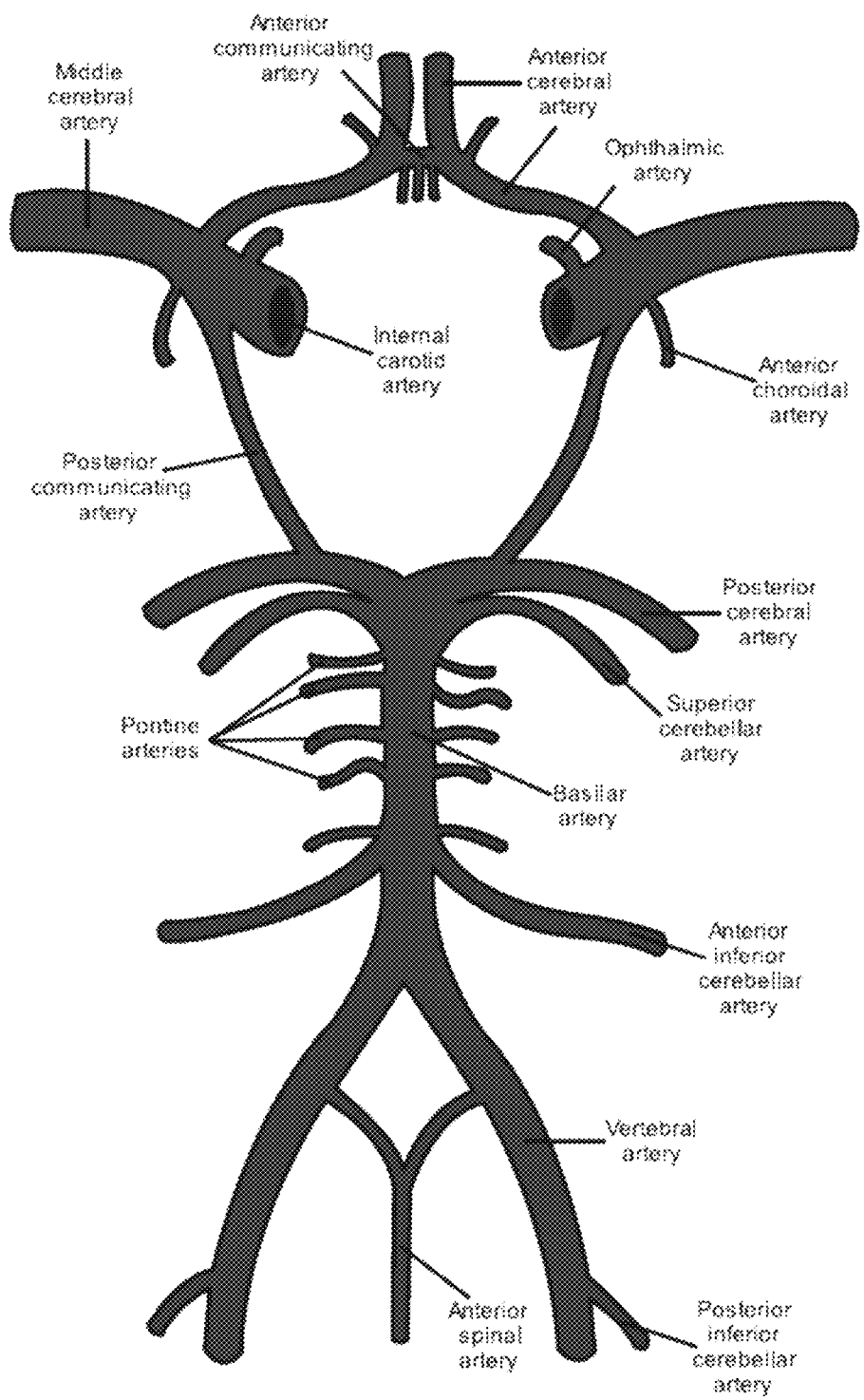
FIG. 1 is a schematic diagram of the main arterial vessels of the brain's vascular anatomy.
Figure 2:
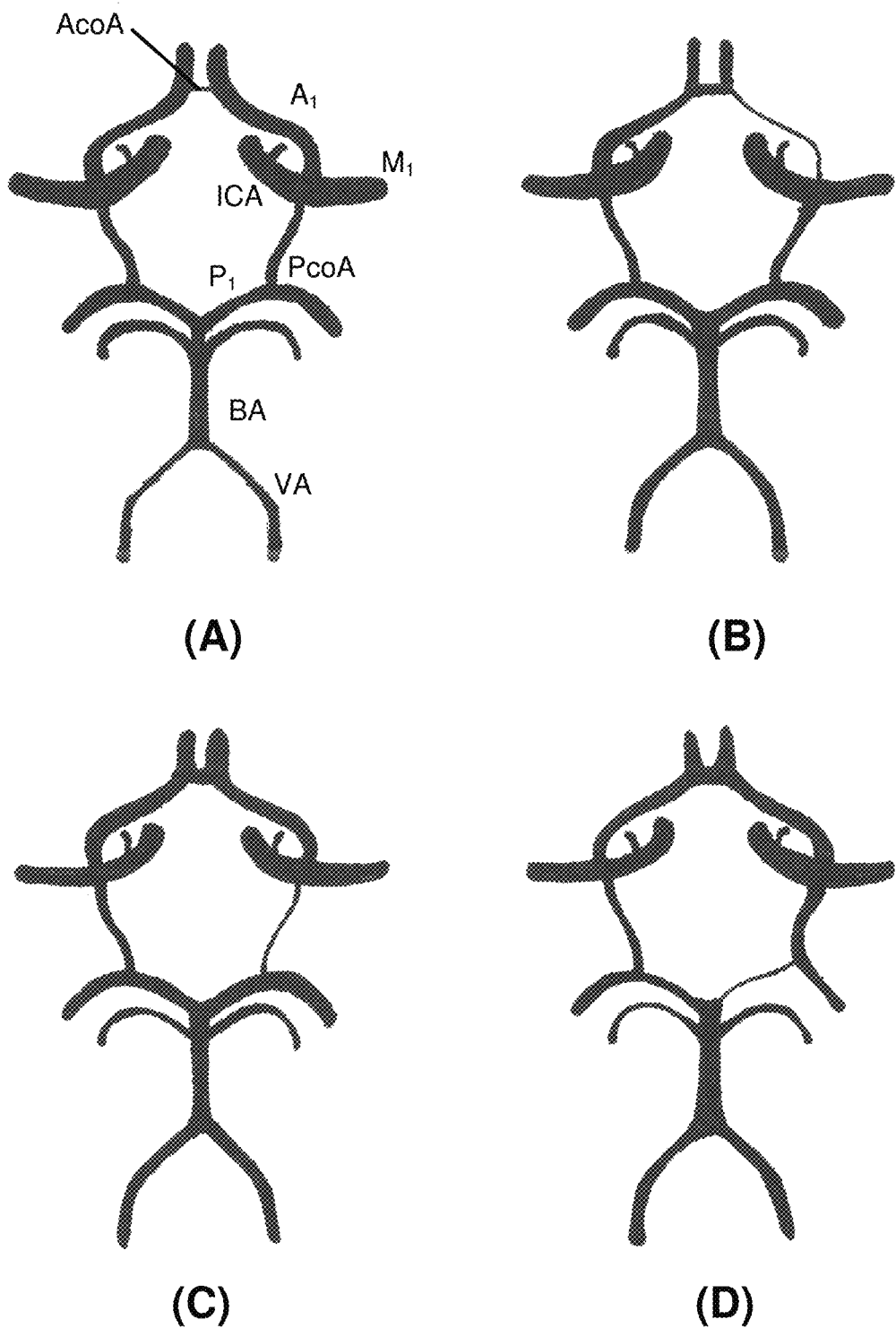
FIG. 2 is a schematic diagram showing typical hypoplastic variations in the Circle of Willis anatomy within the population.

In one embodiment, the pumps and the controller that maintains perfusion flows and pressures is based on predetermined measurements and/or physician based inputs from knowledge of the patient's circulation. Such inputs can include the answers to a series of high level questions that seek to obtain an answer to the effectiveness of circulation within the patient's brain. For example, the physician seeking to determine the degree of ICA circulation may conduct the following analysis:
 a. Is there a possibility of supply to the ipsilateral anterial cerebral artery from the opposite side (FIG. 2A)?
  i. Is the anterior communicating artery (AComA) absent?
  ii. Is the AComA hypoplastic?
 b. Is there further isolation of circulation such that the opposite ACA is also supplied by the ipsilateral ICA (FIG. 2B)?
  i. Is the opposite A1 segment of the ACA absent?
  ii. Is the opposite A1 segment of the ACA hypoplastic?
 c. Is there isolation of the PCA circulation (FIG. 2D)?
  i. fetal PCA with absent P1 segment of PCA?
  ii. fetal PCA with hypoplastic P1 segment of PCA?

Based on these factors an isolation score would be determined, that would typically involve result in a rating representing, for example mild, medium, severe or very severe isolation.

Thereafter, physical parameters would be input. These would generally include:
 a. diameter of the ICA at the high cervical or intracranial level (typically a number between 3.5 and 5 mm).
 b. external diameter of catheter (balloon guide catheter or DAC) (typically a number between 2 and 4 mm).
 c. degree of tortuosity of the vessels (typically, a qualitative rating such as mild, moderate, severe with an associated numeric value). Generally, the greater the tortuosity, the longer it will take to advance the catheter to the M1 segment and the greater the fall in perfusion pressure that would result.
 d. size of the microcatheter inside the DAC.

In addition, other factors including the systemic blood pressure and/or the properties of the liquid being injected may be considered and used as inputs to the controller to determine the rate that a fluid is being injected to maintain perfusion pressure.

That is, based on the various values of the input values (actual numeric values or correlated qualitative measurements), the controller determines and maintains a calculated rate of flow of liquid into the catheter. The boundaries of the model used to determine the upper and lower limits of flow are based on empirical data from research.

As noted, fluids having properties favorable to maintaining collateral circulation and/or neuron nutrition may be injected that may or may not include blood. In cases where total fluid volume may be of concern, blood 40 may be withdrawn from the patient (ie. at the femoral artery access point) and recirculated through the catheter 16.

Figure 9:
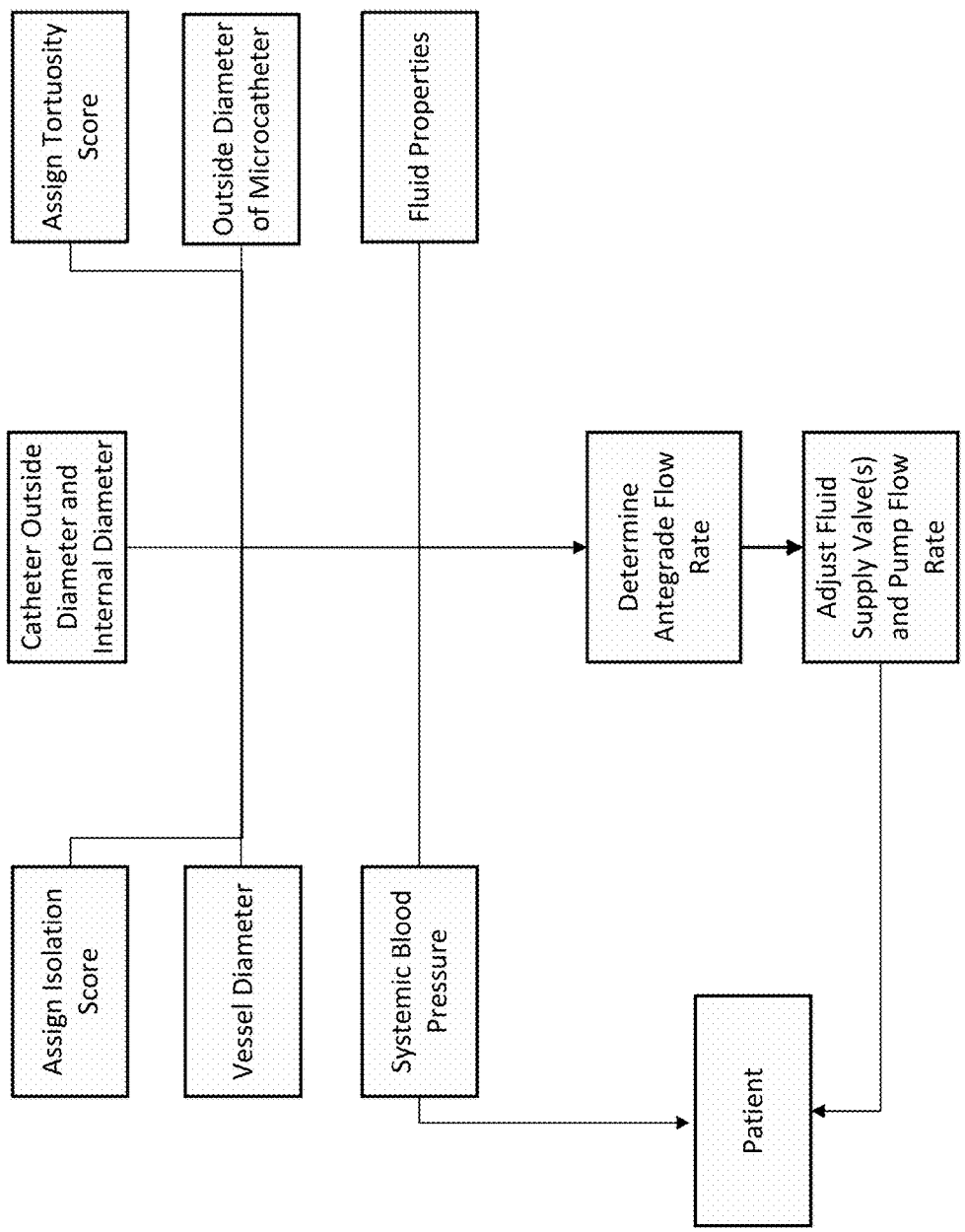
FIG. 9 is a flowchart detailing logical steps in determining the control of antegrade flow into a catheter to maintain collateral flow.

FIG. 9 is a flowchart showing representative inputs used to determine input flow rates. In each case, the inputs may be input to an appropriate input and display system such as any form of known computer. Inputs may be keyed numerical values, values selected from a list of values and/or words that represent a value that are used by the model.

Although the present invention has been described and illustrated with respect to preferred embodiments and preferred uses thereof, it is not to be so limited since modifications and changes can be made therein which are within the full, intended scope of the invention as understood by those skilled in the art.

The invention claimed is:

1. A system to maintain and/or enhance perfusion pressure in a patient with acute stroke and having relatively isolated circulation during an endovascular procedure as a catheter is advancing within the internal carotid artery, the system comprising:
 a catheter adapted for placement within the internal carotid artery, the catheter having a lumen enabling both antegrade and retrograde flow within the lumen, the catheter for operative connection to a pump and controller, the pump and controller for providing selective antegrade flow through the catheter and selective retrograde flow through the catheter at different times during an endovascular procedure where antegrade flow supports collateral perfusion and retrograde flow removes a clot, wherein the controller has means for:
 a. selectively providing antegrade flow through the catheter at a pressure to maintain perfusion pressure;
 b. selectively providing retrograde flow through the catheter at a pressure sufficient to hold and/or withdraw a blood clot through the catheter;
 c. inputting the size of the patient's internal carotid artery and the size of the catheter; and
 d. inputting any one of or combination of:
  i. degree of isolation of circulation;
  ii. size of a microcatheter within the catheter;
  iii. degree of tortuosity of the patient's vasculature;
  iv. systemic blood pressure; and
  v. properties of fluid being injected;
 e. calculating a flow rate of fluid through the catheter sufficient to maintain perfusion pressure based on data from step c; and
 f. pumping the fluid into the catheter at a flow rate calculated in step e.

2. The system as in claim 1, further comprising a fluid supply operatively connected to the pump and controller, where the fluid supply includes anyone of or a combination of isotonic solutions supporting neuron viability including anyone of or a combination of nutrient rich fluids, viscosity reducing fluids, free radical scavengers, neuroprotectants, blood and/or flushing agents.

3. A system to maintain and/or enhance perfusion pressure in a patient with acute stroke and having relatively isolated circulation during an endovascular procedure as a catheter is advancing within the internal carotid artery, the system comprising:
 a pump and controller;
 a catheter configured to be arranged within the internal carotid artery, the catheter having a lumen enabling antegrade flow and retrograde flow within the lumen, the catheter being connected to the pump and controller, the pump and controller being configured to select antegrade flow through the catheter and select retrograde flow through the catheter at different times during an endovascular procedure, wherein the antegrade flow supports collateral perfusion and the retrograde flow removes a clot, wherein the controller has a means for receiving a size of the internal carotid artery of the patient and the size of the catheter as input.

4. A system as in claim 3, wherein the controller is configured to calculate a flow rate of fluid through the catheter sufficient to maintain perfusion pressure based on the input.

5. A system to maintain and/or enhance perfusion pressure in a patient with acute stroke and having relatively isolated circulation during an endovascular procedure as a catheter is advancing within the internal carotid artery, the system comprising:
- a catheter adapted for placement within the internal carotid artery, the catheter having a lumen enabling both antegrade and retrograde flow within the lumen, the catheter for operative connection to a pump and controller, the pump and controller for providing selective antegrade flow through the catheter and selective retrograde flow through the catheter at different times during an endovascular procedure where antegrade flow supports collateral perfusion and retrograde flow removes a clot, wherein the controller is configured to:
  selectively provide antegrade flow through the catheter at a pressure to maintain perfusion pressure;
  selectively provide retrograde flow through the catheter at a pressure sufficient to hold and/or withdraw a blood clot through the catheter;
  receive the size of the internal carotid artery of the patient and the size of the catheter as input;
  receive one or more of degree of isolation of circulation, size of a microcatheter within the catheter, degree of tortuousity of the patient's vasculature, systemic blood pressure; and properties of fluid being injected as input
  calculate a flow rate of fluid through the catheter sufficient to maintain perfusion pressure based on the size of the internal carotid artery of the patient and the size of the catheter; and
  pump the fluid into the catheter at the flow rate.

6. The system as in claim 5, further comprising a fluid supply operatively connected to the pump and controller, where the fluid supply includes anyone of or a combination of isotonic solutions supporting neuron viability including anyone of or a combination of nutrient rich fluids, viscosity reducing fluids, free radical scavengers, neuroprotectants, blood and/or flushing agents.

* * * * *